United States Patent

Holmström

[11] Patent Number: 6,052,622
[45] Date of Patent: Apr. 18, 2000

[54] HEART STIMULATOR WITH AN EVOKED RESPONSE DETECTOR

[75] Inventor: Nils Holmström, Jäfälla, Sweden

[73] Assignee: Pacesetter AB, Järfälla, Sweden

[21] Appl. No.: 09/250,049

[22] Filed: Feb. 12, 1999

[30] Foreign Application Priority Data

Feb. 12, 1998 [SE] Sweden ............................. 9800407

[51] Int. Cl.$^7$ .................................................. A61N 1/362
[52] U.S. Cl. ................................................................ 607/28
[58] Field of Search ............................ 607/27, 28, 9, 607/5

[56] References Cited

U.S. PATENT DOCUMENTS

| | | |
|---|---|---|
| 4,811,738 | 3/1989 | Economides et al. . |
| 5,350,410 | 9/1994 | Kleks et al. . |
| 5,417,718 | 5/1995 | Kleks et al. . |
| 5,431,693 | 7/1995 | Schroeppel . |
| 5,458,623 | 10/1995 | Lu et al. . |
| 5,718,720 | 2/1998 | Prutchi et al. . |
| 5,766,230 | 6/1998 | Routh et al. . |

*Primary Examiner*—Scott M. Getzow
*Attorney, Agent, or Firm*—Hill & Simpson

[57] ABSTRACT

A heart stimulator has a pulse generator for producing stimulation pulses of varying amplitudes and varying durations for stimulating the heart of a patient, and an evoked response detector. The evoked response detector includes measuring and memory circuitry for measuring the charge delivered by a stimulation pulse. The measuring and memory circuitry determine and store, as a reference voltage, a charged voltage value related to the measured charge. Monitoring circuitry monitors the combined polarization and possible evoked response signal picked up from the patient's heart after the delivery of a stimulation pulse and derive a corresponding monitoring voltage value therefrom. A comparator compares the monitoring voltage value to the charged voltage value for determining, from the result of the comparison, the presence or absence of an evoked response.

13 Claims, 4 Drawing Sheets

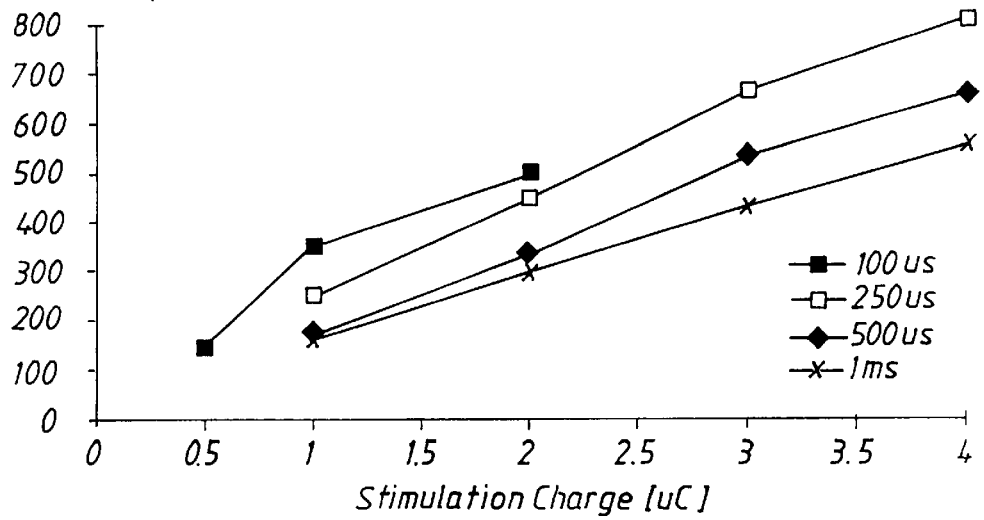
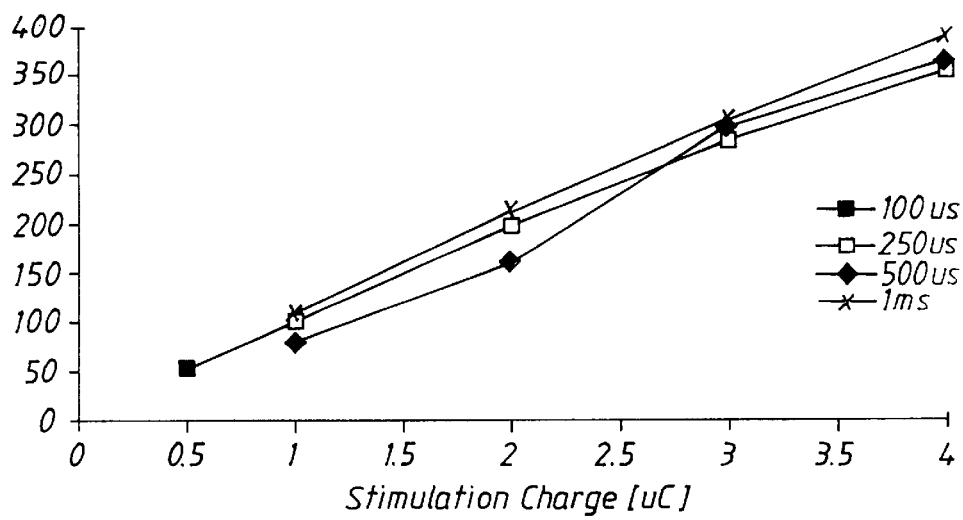

HEART STIMULATOR WITH AN EVOKED RESPONSE DETECTOR

BACKGROUND OF THE INVENTION

1. Field of the Invention

The present invention relates to an evoked respons detector for a heart stimulator for determining evoked response In the presence of polarization, the heart stimulator being of the type having a pulse generator for producing stimulation pulses of varying amplitudes and varying durations for stimulating the heart of a patient, and the evoked response detector having measuring and memory means for measuring the charge delivered by a stimulation pulse, The invention also relates to a heart stimulator having such an evoked response detector.

2. Description of the Prior Art

There is a need to make unipolar pacemakers, both for ventricular and atrial stimulation of the heart of a patient, that have a so-called AUTOCAPTURE™ pacing system function, The AUTOCAPTURE™ function is used to maintain the energy of the stimulation pulse at a level just above the level which is needed to effectuate capture, described, for example, in U.S. Pat. No. 5,458,623. In this context it is difficult to detect evoked response in a safe and reliable manner, since the evoked response potential is small in amplitude compared to the residual polarization after the stimulation pulse and this polarization is varying when the stimulation energy is varied for the threshold search. The polarization is also varying with variations of the impedance.

Several attempts have been made to solve the polarization problems in connection with evoked response detection. Thus U.S. Pat. No. 5,417,713 discloses a system for maintaining capture, wherein an electrical post-stimulus signal of the heart following delivery of a stimulation pulse is compared to a polarization template, determined during a capture verification test. A prescribed difference between the polarization template and the post-stimulus signal then indicates capture. Otherwise loss of capture is presumed and the stimulation energy is increased a predetermined amount to obtain capture.

One technique of reducing the effects of polarization is to remove the polarization charge by supplying after the delivery of the stimulation pulse one or more suitable pulses of opposite polarity, see U.S. Pat. No. 4,811,738.

U.S. Pat. No, 5,431,693 describes a method for verifying capture by a pacemaker. This method is based on the observation that the non-capture potential is exponential in form and the evoked capture potential, while generally exponential in form, has one or more small-amplitude perturbations superimposed on the exponential wave form. These perturbations are enhanced for facilitating detection by processing the waveform signal by differentiation to form the second derivative of the evoked response signal for analysis for the evoked response detection.

Unipolar detection of evoked response signals is, however, not possible by this technique. Abrupt slope changes or superimposed small-amplitude perturbations are leveled out when the measurements are made over a longer distance from the electrode to the stimulator casing. In Swedish patent application No. 9703600-8 (corresponding to pending U.S. application Ser. No. 09/161,665 filed Sep. 29, 1998 ("Heart Stimulator With An Evoked Response Detector," Budgifvars et al.,) and European Application 98116180.5) an evoked response detector is described which functions based on the fact that the evoked response signal amplitude does not vary significantly with the amplitude of the stimulation pulse (provided that the stimulation amplitude is above the capture threshold) whereas the electrode polarization is approximately linearly dependent on the stimulation pulse amplitude for a constant pulse duration within a certain stimulation pulse amplitude range. This constancy versus linear dependency dichotomy is used to distinguish the evoked response signal from the polarization signal.

SUMMARY OF THE INVENTION

Experiments have now shown that polarization of stimulation electrodes is proportional to the charge of the delivered stimulation pulse. An object of the present invention is to provide an improved detector for determining evoked response based on this discovery, which makes detection of evoked response possible with the aid of unipolar as well as bipolar stimulation electrodes, implanted in the ventricle or in the atrium of the heart of a patient. The purpose of the invention is also to provide a heart stimulator equipped with such a detector.

The above object is achieved in accordance with the principles of the present invention in a heart stimulator having an evoked response detector containing measuring and memory means for measuring a charge delivered to a heart by a stimulation pulse, the measuring and memory means storing, as a reference voltage, a charge voltage value, a monitoring circuit for monitoring the incoming combination of the polarization signal and, if present, the evoked response signal obtained from the patient's heart after the delivery of a stimulation pulse, the monitoring circuit deriving a monitoring voltage value from this combination, and a comparison circuit for comparing the monitoring voltage value with the charge voltage value and for determining, dependent on the result of the comparison, the presence or absence of an evoked response.

Thus, in the detector according to the invention the charge of a stimulation pulse is measured and a corresponding charge voltage value is determined as a reference value, and the polarization and possible evoked response signal is monitored after delivery of the stimulation pulse and compared to this reference value for determining the presence or absence of an evoked response. In this way evoked responses can be reliably detected for stimulation pulses of varying output energies e.g. during a threshold search by eliminating the influence of varying polarization on the detected cardiac evoked response. By using the measured delivered charge in this way for compensating for the polarization of the evoked response signal, it is possible to create a fully automatic evoked response detector for all kinds of uni- and bipolar electrodes, for all stimulation pulse amplitudes and every possible pulse duration. The detector is especially useful for stimulation threshold search when pulse duration or pulse amplitude or both these parameters are changed at the same time. Also variations of the lead impedance are compensated without a need to manually adjust the detector settings.

According to an embodiment of the detector according to the invention the measuring and memory means determine the charge voltage value $U_D$ by the relation $$U_D = k \cdot Q + m$$

wherein k denotes a variable factor chosen such that $U_D$ is equal to the measured polarization with m=0, Q is the charge of a stimulation pulse, and m is an evoked response detection voltage margin. In this way the charged voltage value $U_D$ can be automatically determined by adjusting the factor k by tuning of an amplifier gain.

According to another embodiment of the detector according to the invention, the evoked response detection voltage margin m is proportional to the charged voltage value $U_D$. This is an important feature for maintaining a detection voltage margin m of constant relative magnitude. If the evoked response voltage margin m were equal to a constant value, the detection voltage margin m would be relatively higher for low voltage values $U_D$ than for high values.

According to another embodiment of the detector according to the invention the monitoring means determine the monitoring voltage value equal to a value of the combined polarization and possible evoked response signal sampled at a predetermined time after delivery of the stimulation pulse. The sampling operation is then preferably performed at a time when the best evoked response signal is expected. This time can typically be about 2 ms after the beginning of the stimulation pulse.

According to another embodiment of the detector according to the invention, the monitoring means determine the monitoring voltage value $U_B$ by integrating the voltage signal $U_A(t)$ picked up from the patient's heart over a predetermined time interval after delivery of the stimulation pulse The potential of the stimulation electrode is then integrated over a time interval in which a good reproducible evoked response signal is expected. This is a reliable method for determining evoked response which allows large individual morphology variations in the evoked response signal.

According to another embodiment of the detector according to the invention, the comparison means indicate evoked response if the monitoring voltage value $U_B$ exceeds the charged voltage value $U_D$. If this condition is not fulfilled, loss of capture is indicated.

In an embodiment of a heart stimulator according to the invention, the pulse generator is controlled to deliver stimulation pulses at amplitudes which are as high as possible without the use of voltage doubling means. Since the stimulation charge threshold decreases with decreasing pulse duration (see e.g. Furman, "A Practice of Cardiac Pacing", Second edition, Futura Publishing Company, New York, 1989, pp. 42–49) the polarization at the stimulation threshold is lower for a shorter pulse width. The battery current drain for stimulation at the threshold is also lower for shorter pulses as long as the stimulation amplitude is below the battery voltage of the stimulator. Therefore, it is recommended to stimulate with the highest voltage possible that does not require voltage doubling means, i.e., 2.8 V in practice, and consequently to reduce the pulse width toward the duration threshold. If so, the evoked response sensing will be facilitated and current consumption will be minimal. This is further discussed in connection with tissue stimulation in general in U.S. Pat. No. 5,391,191.

According to another embodiment of the heart stimulator according to the invention, a microprocessor stores and analyzes data as to detected polarization and evoked response threshold variations. From this data electrode micro-dislocations and other electrode lead disorders can be ascertained.

DESCRIPTION OF THE DRAWINGS

FIG. 1 shows the relation between the measured polarization and the respective charges of stimulation pulses of different pulse widths measured directly after emission of the stimulation pulse.

FIG. 2 shows the relation between the measured polarization and the respective charges of stimulation pulses of different pulse widths measured 2 ms after the beginning of each stimulation pulse.

DESCRIPTION OF THE PREFERRED EMBODIMENTS

FIGS. 1 and 2 show the results of in vitro measurements of the polarization as a function of the charge (in micro-Coulombs µc) of stimulation pulses for pulses of varying widths. The polarization voltage was measured in a physiological saline solution, a so-called Ringer solution, between a tip electrode and an indifferent electrode. FIG. 1 shows the result of measurements performed directly after the termination of the stimulation pulse and FIG. 2 shows the result of measurements following 2 ms after the beginning of the stimulation pulse. The width of the stimulation pulse is typically somewhat less than 0.5 ms. In FIG. 1 a somewhat lower polarization was measured for wide pulses than for short ones for equal stimulation charge. This is due to the fact that polarization from the beginning of the stimulation pulse has decreased for wide pulses. FIG. 2 shows a good linear relationship between the polarization and the delivered charge of stimulation pulse, independently of the pulse width. This linear relationship between polarization and stimulation charge is used in the detector according to the invention.

Figure 3:
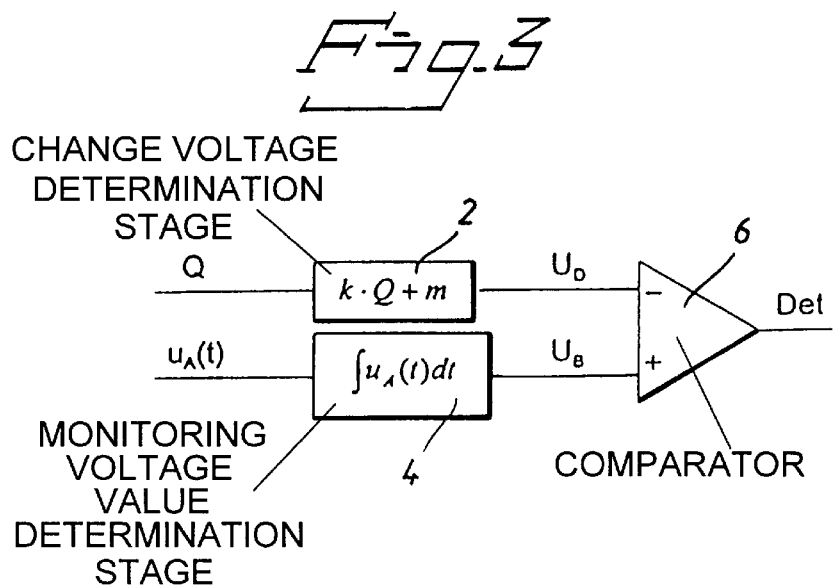
FIG. 3 is a block diagram illustrating an embodiment of an evoked response detector according to the invention.

In the detector according to the invention the charge Q delivered by a stimulation pulse is measured and stored on one channel. The resulting polarization together with a possible evoked response after the stimulation pulse uA(t) is monitored on another channel (see FIG. 3). The charge Q is processed to a corresponding voltage value according to the equation $$U_D = k \cdot Q + m \tag{1}$$

wherein k is a variable factor chosen to be equal to the measured polarization with m equal to 0. The charge voltage value $U_D$ is determined in a charge voltage determination stage 2 in FIG. 3 and forms a reference value for a subsequent comparison. The factor k has the nature of a gain and the determination or tuning of the factor k can be performed automatically as will be described below. The variable m denotes an evoked response detection margin and is preferably proportional to the amplitude of the voltage $U_D$, as mentioned above. If m were chosen to be a constant, its relative magnitude should be much larger for low amplitudes than for high ones. The detection margin m is chosen low enough for avoiding undersensing, i.e. making the detector too insensitive for the detection of evoked response signals, but high enough to depress noise and polarization variations, i.e. for avoiding oversensing of the detector. Thus with a detector according to the invention the detection margins for evoked response undersensing and evoked response oversensing can be continuously followed after each stimulation pulse without losing capture.

A monitoring voltage value $U_B$ can be determined, in a monitoring voltage value determination stage 4, from the combined polarization and evoked response signal $U_A(t)$ in at least two different ways.

The voltage $U_B$ can be determined by sampling the potential of the stimulation electrode at a specified time $t_x$ after the stimulation, preferably at a time when the best evoked response signal is expected.

An alternative way of determining the voltage $U_B$ is to integrate the polarization and possible evoked response signal $U_A(t)$ over a time interval after the stimulation pulse when a good reproducible evoked response signal is expected, e.g., at 2 ms after the beginning of the stimulation pulse, cf. the discussion of FIG. 2. This latter way of determining the voltage value $U_B$ is indicated in the monitoring voltage value determination stage 4 shown in FIG. 3 and allows large individual evoked response morphology variations and is more reliable than the above-mentioned sampling procedure.

The two voltages $U_D$ and $U_B$ are then compared in a comparator 6, and if $U_B > U_D$, detection of evoked response is indicated, otherwise loss of capture is indicated.

Figure 4:
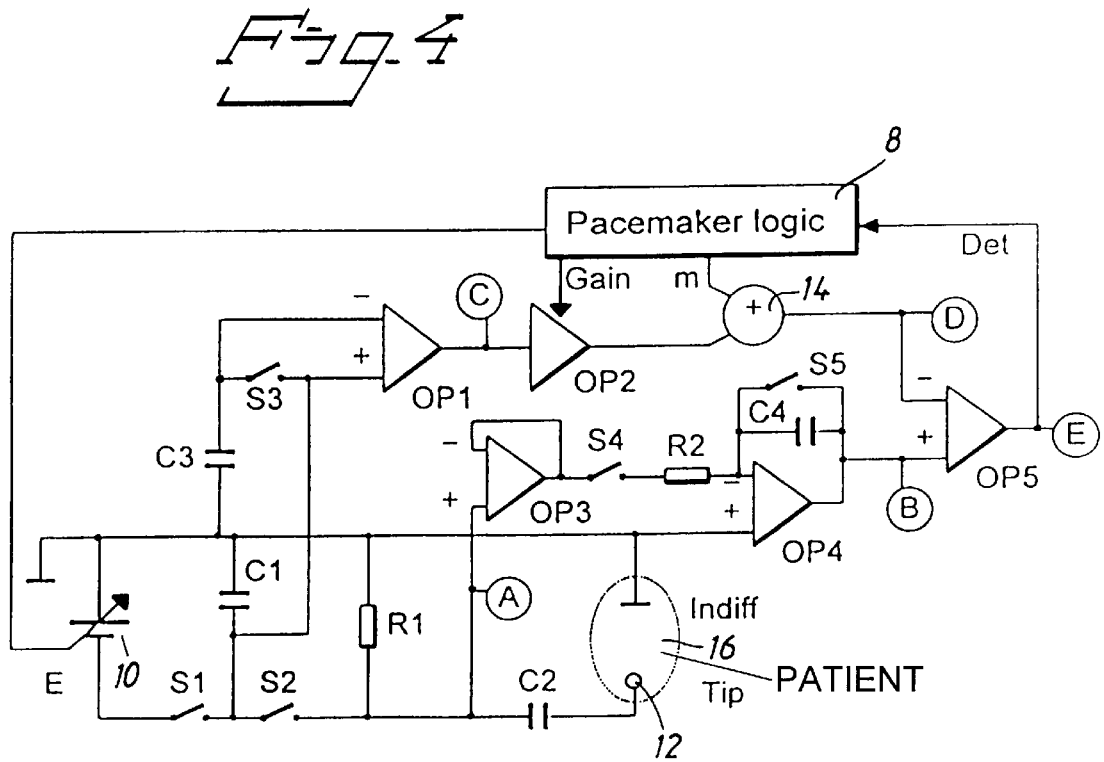
FIG. 4 shows an embodiment of electronic circuitry for a heart stimulator according to the invention, embodying an evoked response detector as shown in FIG. 3.

FIG. 4 shows an example of the electronic circuitry of a heart stimulator according to the invention including an evoked response detector as described above. For the explanation of the operation of the stimulator, reference is also made to the timing diagram in FIG. 5. The curves Pol and ER following the stimulation pulse in the uA-time diagram in FIG. 5 represent the polarization signal and the combined polarization and evoked response signal, respectively.

Figure 5:
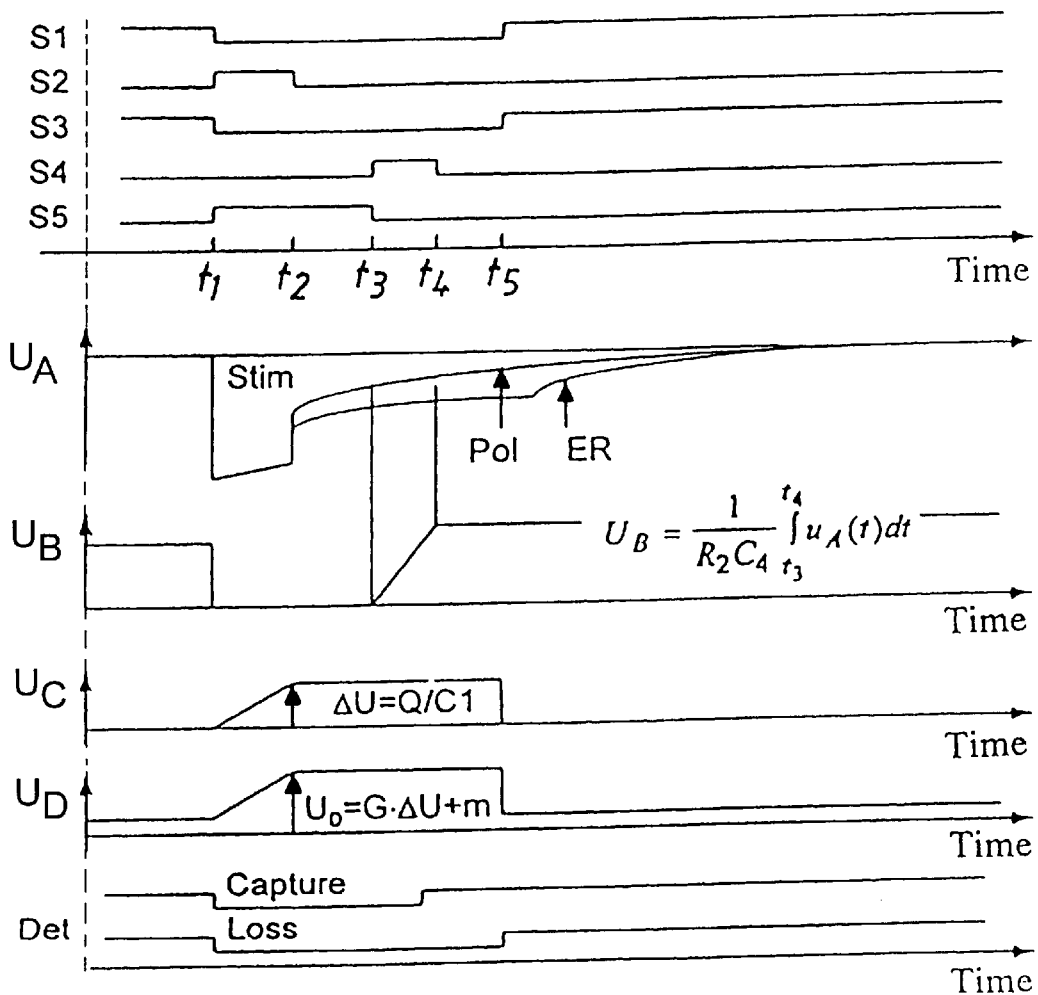
FIG. 5 is a timing diagram illustrating the operation of the heart stimulator of FIG. 4 in a first mode of operation.

From the pacemaker logic unit 8, the voltage F of the variable voltage source 10 is adjusted to be equal to the desired stimulation amplitude in the time interval $t_5-t_1$ in FIG. 5, between the stimulation pulses. In this phase the switches S1 and S3 are closed and the capacitors C1 and C3 are charged to the voltage F.

At time $t_1$ the switches S1 and S3 are opened and switch S2 is closed and a stimulation pulse is delivered to the electrode tip 12 implanted in a patient 16.

The switch S5 is also closed at this time to reset the voltage on the capacitor C4 for the next evoked response detection. During the stimulation phase the capacitor C1 is discharged while the voltage or the capacitor C3 remains unchanged. Amplifier OP1 is an instrumental amplifier with unity gain, and its output voltage $U_C$ will increase during the stimulation pulse proportionally to the delivered charge Q and at the time $t_2$ the voltage $U_C$ has reached the level Q/C1 (see FIG. 5). This voltage $U_C$ is amplified with a gain factor G in the amplifier OP2 and a voltage value m is added in the adder 14 to form the voltage $$U_D = G \cdot Q/C1 + m \quad (2)$$

This voltage $U_D$ is constant between the time $t_2$ and $t_5$, cf. FIG. 5. and constitutes the charged voltage value used as reference for subsequent evoked response detection. The detection margin m is delivered by an AD-converter in the pacemaker logic unit 8.

Between the times $t_3$ and $t_4$ the switch S4 is closed and the sensed polarization and evoked response signal is integrated on the capacitor C4 according to the equation $$U_B = \frac{1}{R_2 C_4} \int_{t_3}^{t_4} u_A(t) \, dt \quad (3)$$

where $R_2$ denotes an input resistance to amplifier OP4.

The voltages $U_D$ and $U_B$ are compared in the comparator OP5 and the indication for capture is that $U_B > U_D$ in the time window between $t_4$ and $t_5$, see FIG. 5.

By increasing the magnitude of the detection margin m until the comparator $OP_5$ toggles directly after detection of capture, it is possible to test the evoked response amplitude margin m.

The output signal from the comparator OP5, indicating whether evoked response is detected, is supplied to the pacemaker logic unit 8 for controlling the continued operation of the heart stimulator.

With microprocessor techniques, data regarding polarization and threshold variations can be stored and analyzed in the heart stimulator according to the invention, i.e., for identifying electrode micro-dislocations and other lead irregularities.

One preferred way of setting the above mentioned gain G, cf. equation (2), will now be described.

Figure 6:
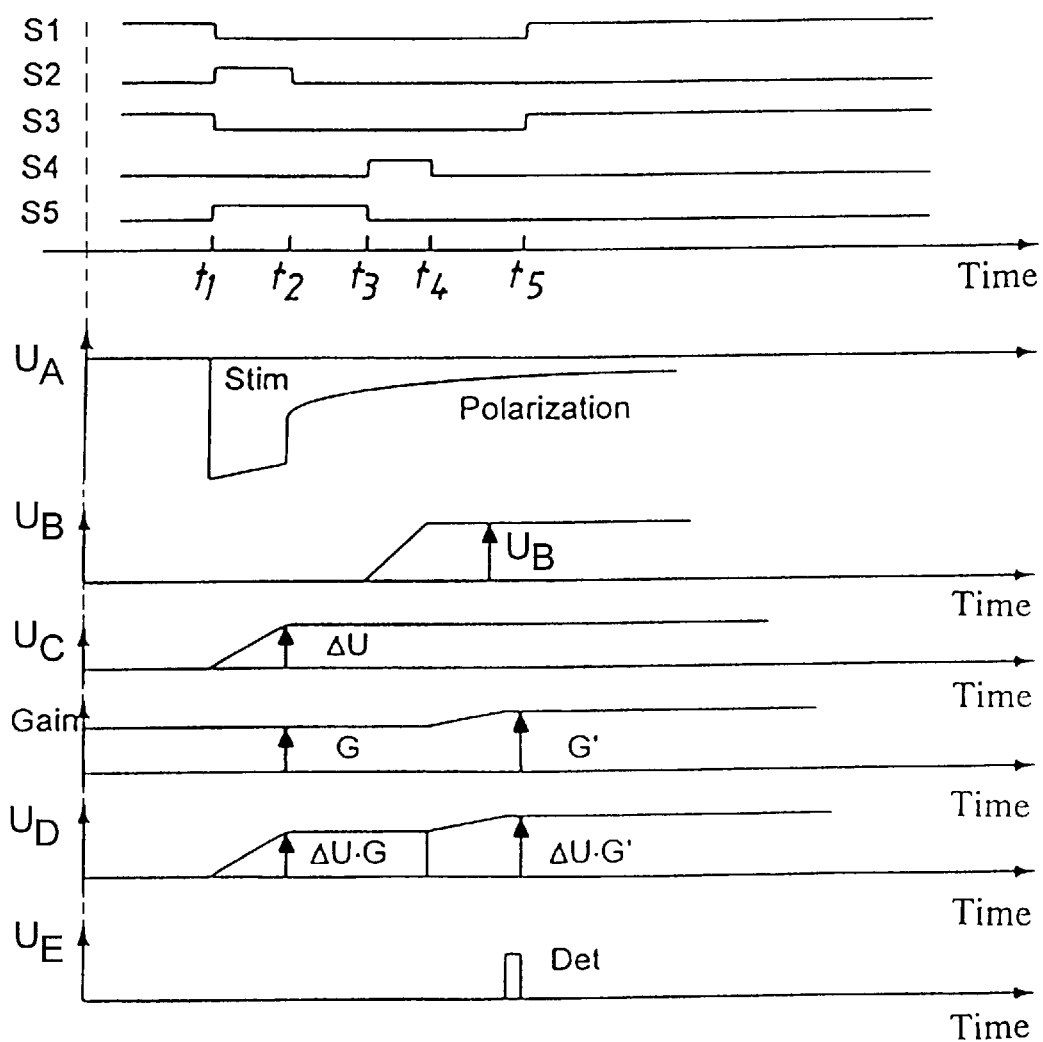
FIG. 6 is a timing diagram illustrating the operation of the heart stimulator of FIG. 4 in a second mode of operation.

A stimulation pulse is then delivered in the refractory period of the patient's heart or a pulse below the stimulation threshold is delivered. No evoked response signal is then added to the voltage signal $U_A$, sensed on the node A in FIG. 4. Thus the sensed voltage $U_A$ just represents the polarization, see FIG. 6. Between the times $t_3$ and $t_4$ the polarization from the preceding stimulation pulse is integrated on the capacitor C4. This voltage $U_B$ is held on node B from the time $t_4$ until the switch S5 is closed again.

The charge delivered during a stimulation pulse amounts to $$Q = C1 \cdot \Delta U$$

wherein $\Delta U$ is the voltage on node $C_1$ which is constant after time $t_2$. The amplification gain G of the programmable amplifier OP2 is then adjusted by the pacemaker logic unit 8 so that the amplifier output voltage equals the voltage on node B ($G' \cdot \Delta U = U_B$). This condition is fulfilled when the comparator OP5 toggles and an output pulse $U_E$ is obtained on the output of the comparator OP5, cf, FIG. 6. During this calibration procedure the m-value is set equal to zero.

Since the polarization is proportional to the delivered charge for all pulse widths and amplitudes, the new amplification factor G' can be used for any pulse configuration thereafter to distinguish between capture and loss of capture. To get a defined detection margin m in Volt, $U_D$ is increased with a constant value of m applied from the pacemaker logic unit 8. The new reference voltage on node D is then equal to $G' \cdot U + m$, and if the integrated polarization on node B after a stimulation pulse is higher than the above mentioned reference voltage, capture is detected, otherwise the stimulation resulted in a loss of capture.

An alternative method of determining the gain factor G is stimulation with two different output charges Q1 and Q2, both these charges being above the stimulation threshold and both resulting in capture. The gain for both stimulation pulses is then adjusted, with the stimulation margin m set equal to 0, by the pacemaker logic unit 8, such that the comparator OP5 just toggles. Since the polarization signal will be proportional to the charge of the stimulation pulses, whereas the evoked response signal is independent of the charge, it is possible to calculate the gain factor C. Thus the following equations are valid.

$$U_B(Q1) = K^*Q1 + ER = G1^*Q1/C1 \quad (4)$$

$$U_B(Q2) = K^*Q2 + ER = G2^*Q2/C1 \quad (5)$$

From these equations (4) and (5) the quantity K is obtained as $$K = \frac{G1 \cdot Q1 - G2 \cdot Q2}{C1(Q1 - Q2)} \quad (6)$$

wherein G1 and G2 denote the adjusted gains for the two stimulation pulses and ER denotes the evoked response signal. For ER=0 the following equation is valid $$U_B(Q) = K*Q = G*Q/C1 \quad (7)$$

By eliminating the quantity K between the above equations (6) and (7) the following expression is obtained for the desired gain G $$G = \frac{G1 \cdot Q1 - G2 \cdot Q2}{Q1 - Q2} \quad (8)$$

When the desired gain G is known it is just to use the actual setting for the next evoked response measurement.

Although modifications and changes may be suggested by those skilled in the art, it is the intention of the inventor to embody within the patent warranted hereon all changes and modifications as reasonably and properly come within the scope of his contribution to the art.

I claim as my invention:

1. A heart stimulator comprising:

a pulse generator which emits a series of stimulation pulses each having a pulse width and an amplitude, the respective pulse widths and amplitudes of said stimulation pulses being variable from stimulation pulse-to-stimulation pulse, and each stimulation pulse having a charge associated therewith;

an electrode system connected to said pulse generator for delivering said stimulation pulses in vivo to a heart and for picking up a combined signal comprising a polarization signal and, if present, an evoked response following each of said stimulation pulses;

measuring and memory means for measuring the charge associated with a stimulation pulse as said stimulation pulse is emitted and for storing, as a reference voltage, a charge voltage value related to said charge;

monitoring means, connected to said electrode system, for deriving a monitoring voltage value from said combined signal;

a comparator supplied with said monitoring voltage value and said charge voltage value for comparing said monitoring voltage value and said charge voltage value and for producing a comparison result indicating whether an evoked response is present in said combined signal; and control means for controlling said pulse generator to vary at least one of said pulse width and said pulse amplitude dependent on said comparison result.

2. A heart stimulator as claimed in claim 1 wherein said measuring and memory means comprises means for determining said charge voltage value according to a relation $$U_D = k \cdot Q + m$$

wherein k is a variable factor, Q is said charge of a stimulation pulse, m is an evoked response detection voltage margin, and $U_D$ is said charge voltage value.

3. A heart stimulator as claimed in claim 2 wherein said measuring and memory means comprises means for selecting said variable factor k such that said charge voltage value $U_D$ is equal to said polarization signal with said evoked response detection voltage margin m=0.

4. A heart stimulator as claimed in claim 2 wherein said evoked response detection voltage margin is proportional to said charge voltage value $U_D$.

5. A heart stimulator as claimed in claim 2 wherein said measuring and memory means comprises means for setting said variable factor k comprising an amplifier with an adjustable gain for amplifying said charge voltage value $U_D$ without said evoked response detection margin m so that said charge voltage value $U_D$ becomes equal to said monitoring voltage value obtained from said combined signal resulting from a stimulation pulse delivered in a refractory period of said heart.

6. A heart stimulator as claimed in claim 2 wherein said measuring and memory means comprises means for setting said variable factor k comprising an amplifier with an adjustable gain for amplifying said charge voltage value $U_D$ without said detection margin m obtained from a stimulation pulse with an energy below a stimulation threshold of said heart, so that said charge voltage value $U_D$ becomes equal to said monitoring voltage value obtained from said stimulation pulse below said stimulation threshold.

7. A heart stimulator as claimed in claim 2 wherein said measuring and memory means comprises means for setting said variable factor k comprising an amplifier with an adjustable gain for amplifying said charge voltage value $U_D$ without said detection margin m so that said charge voltage value $U_D$ becomes equal to said monitoring voltage value for two stimulation pulses of respectively different charges above an evoked response threshold of said heart resulting in capture, and further comprising means for calculating, from said different charges and from respective adjusted gains of said amplifier for said two stimulation pulses, a gain of said amplifier which is used for setting said charge voltage value $U_D$ for a next evoked response measurement.

8. A heart stimulator as claimed in claim 1 further comprising an analog-to-digital converter which generates said evoked response detection voltage margin.

9. A heart stimulator as claimed in claim 1 wherein said monitoring means comprises means for setting said monitoring voltage value equal to a value of said combined signal sampled at a predetermined time after delivery of a stimulation pulse.

10. A heart stimulator as claimed in claim 1 wherein said monitoring means comprises means for determining said monitoring voltage value by integrating said combined signal over a predetermined time interval after delivery of a stimulation pulse.

11. A heart stimulator as claimed in claim 1 wherein said comparator produces a comparison result indicating a presence of an evoked response if said monitoring voltage value exceeds said charge voltage value.

12. A heart stimulator as claimed in claim 1 wherein said pulse generator comprises means for generating said stimulation pulses with as high an amplitude as possible without using a voltage doubling circuit.

13. A heart stimulator as claimed in claim 1 wherein said measuring and memory means, said monitoring means and said comparator comprise a microprocessor.

* * * * *